US00PP28966P2

(12) United States Plant Patent
Benetka

(10) Patent No.: US PP28,966 P2
(45) Date of Patent: Feb. 20, 2018

(54) ***WEIGELA* PLANT NAMED 'VUKOZ053929'**

(50) Latin Name: *Weigela hybrida*
Varietal Denomination: VUKOZ053929

(71) Applicant: Vojtech Benetka, Chodov (CZ)

(72) Inventor: Vojtech Benetka, Chodov (CZ)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/330,182

(22) Filed: Aug. 18, 2016

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Anne M Grunberg
(74) *Attorney, Agent, or Firm* — Cassandra Bright

(57) ABSTRACT

A new and distinct *Weigela* plant named 'VUKOZ053929' is disclosed, characterized by rich flowering and reblooming of white flowers with a yellow patch in the middle. The new variety is a *Weigela*, normally produced as an outdoor garden plant.

3 Drawing Sheets

Latin name of the genus and species: *Weigela hybrida.*
Variety denomination: 'VUKOZ053929'.

BACKGROUND OF THE INVENTION

The new *Weigela* cultivar is a product of a planned breeding program conducted by the inventor, Vojtech Benetka, in Pruhonice, Czech Republic. The objective of the breeding program was to produce new *Weigela* varieties with white flowers. The cross resulting in this new variety was made in 2005.

The seed parent is a proprietary, unpatented, unnamed *Weigela* referred to as '02-6-189'. The pollen parent is the proprietary unpatented, unnamed *Weigela* '02-7-265'. The new variety was identified as a potentially interesting selection in 2008, at a research nursery in Pruhonice, Czech Republic.

Asexual reproduction of the new cultivar 'VUKOZ053929' by softwood cuttings was first performed in 2008, at a research nursery in Pruhonice, Czech Republic. Subsequent propagation has shown that the unique features of this cultivar are stable and reproduced true to type in five successive generations.

SUMMARY OF THE INVENTION

The cultivar 'VUKOZ053929' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VUKOZ053929' These characteristics in combination distinguish 'VUKOZ053929' as a new and distinct *Weigela* cultivar:

1. White flowers with a yellow center.
2. Rich flowering.
3. Re-blooming.

PARENT COMPARISON

Plants of the new cultivar 'VUKOZ053929' are similar to plants of the seed parent in most horticultural characteristics, however, plants of the new cultivar 'VUKOZ053929' differ in the following;

1. New cultivar has white flowers with a yellow center, whereas the parent has light pink flowers.

Plants of the new cultivar 'VUKOZ053929' are similar to plants of the pollen parent in most horticultural characteristics, however, plants of the new cultivar 'VUKOZ053929' differ in the following;

1. New cultivar has white flowers with a yellow center, whereas the parent has white flowers.

COMMERCIAL COMPARISON

Plants of the new cultivar 'VUKOZ053929' can be compared to the unpatented commercial variety *Weigela* 'Bokrasopea' (U.S. Plant Pat. No. 24,585). These varieties are similar in most horticultural characteristics; however 'VUKOZ053929' differs in the following:

1. New cultivar has white flowers with a yellow center whereas the commercial variety has white flowers with a slight yellow center which fade to light pink.
2. New cultivar has larger flowers than the commercial comparison.

BRIEF DESCRIPTION OF THE PHOTOGRAPHS

The accompanying photograph in FIG. 1 illustrates in full color a side view perspective of a typical plant of 'VUKOZ053929' grown in a 1 gallon pot.

Figure 1:
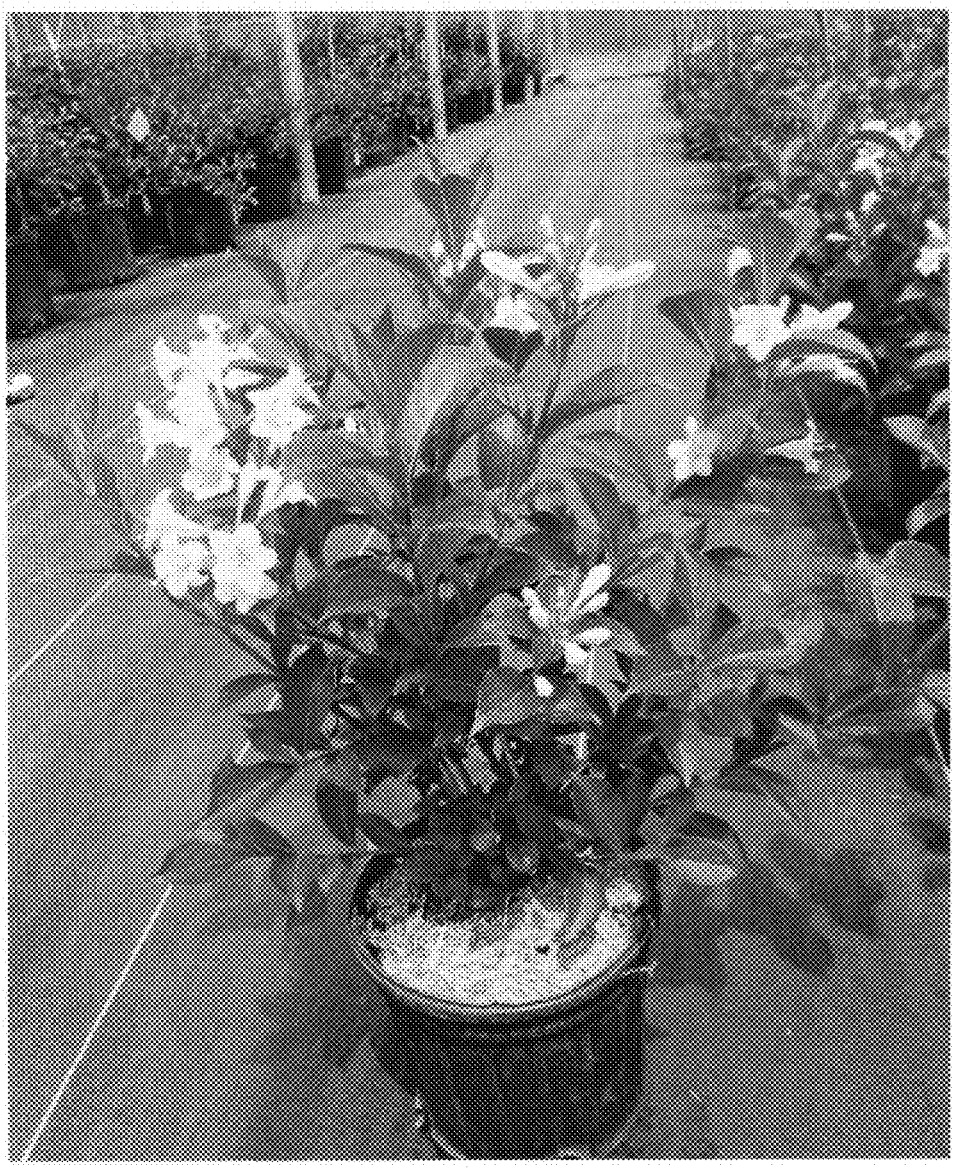
Figure 2:
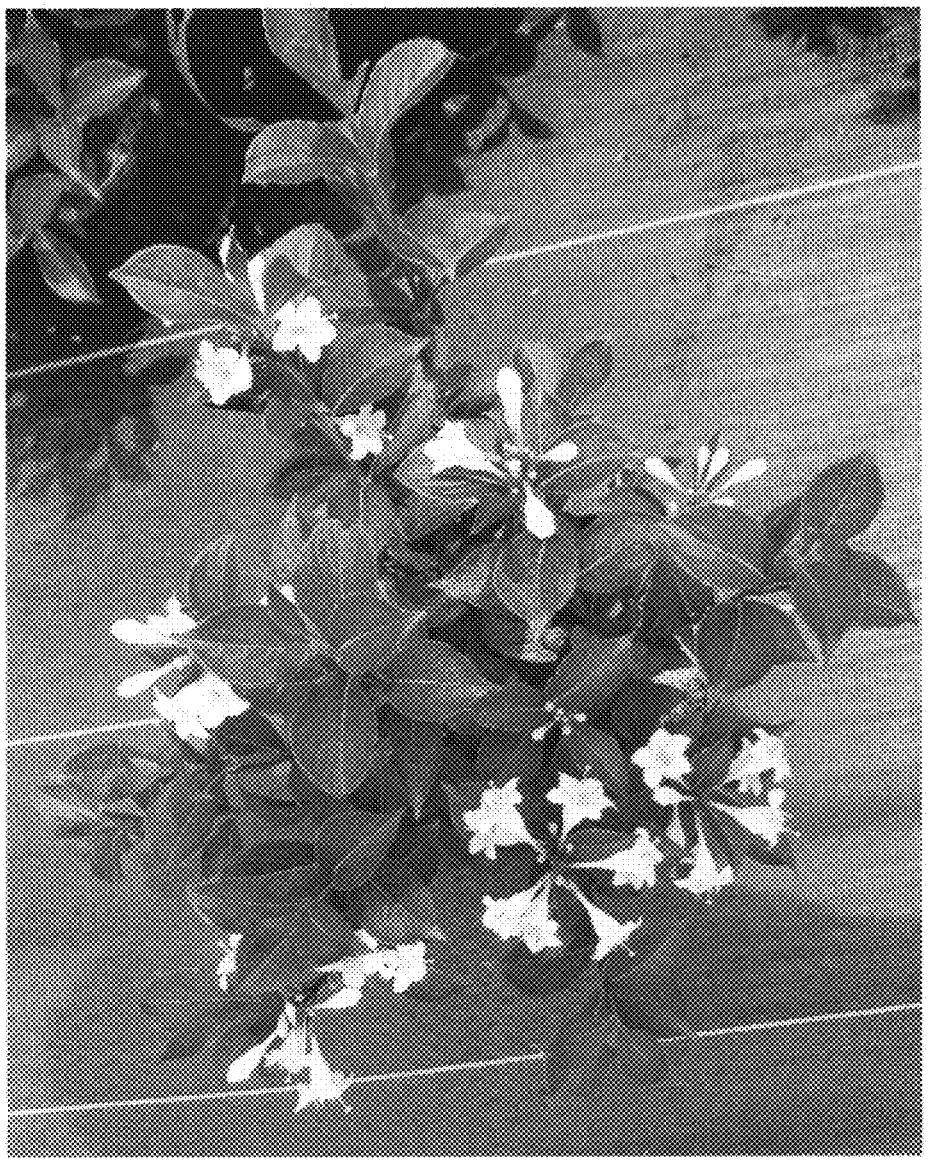
FIG. 2 illustrates the same plant with an overhead perspective. Age of the plant photographed is approximately 2 years.
Figure 3:
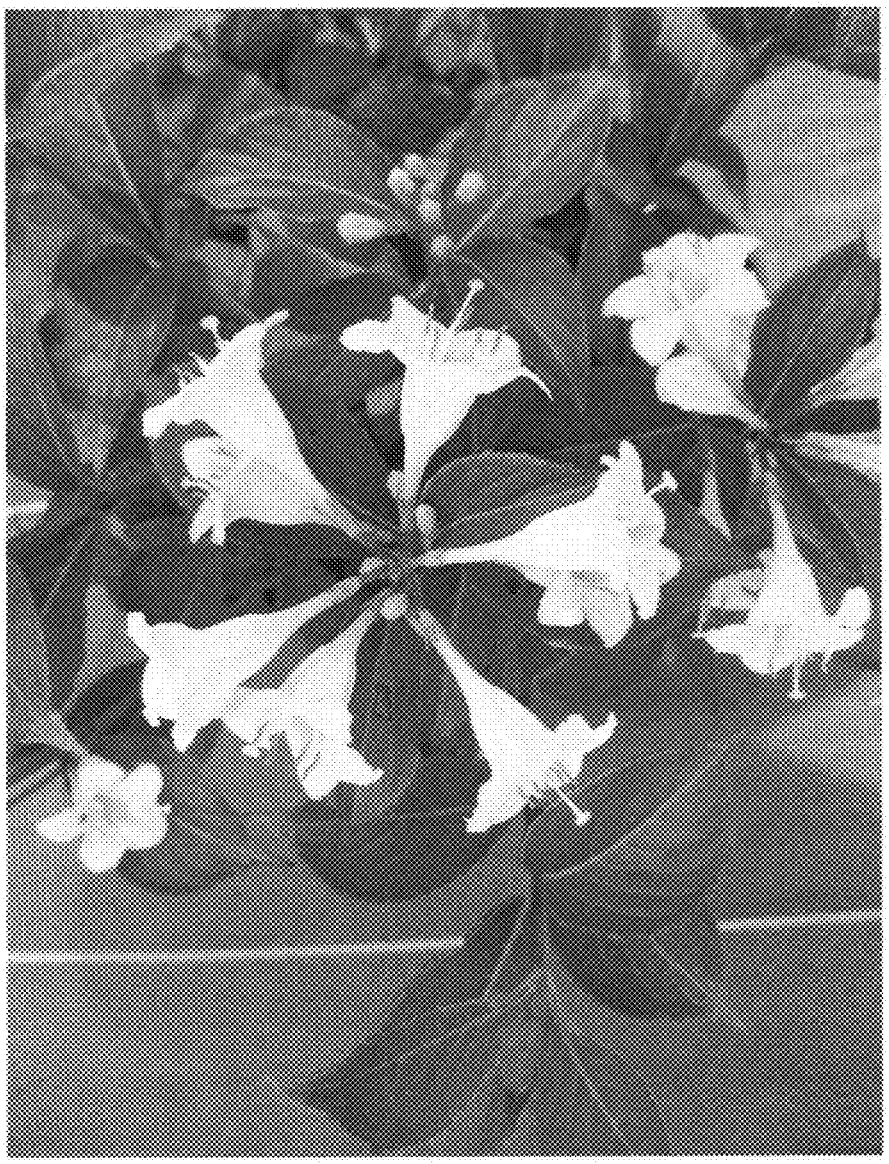
FIG. 3 illustrates a close-up view of the inflorescence and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'VUKOZ053929' plants grown in a polyhouse in Grand Haven, Mich. Measurements were taken during late Spring. The plants were 2 years old. The growing temperature ranged from approximately 5° C. to 27° C. Measurements and numerical values represent averages of typical plant types.

Botanical classification: *Weigela hybrida* 'VUKOZ053929'.

PROPAGATION

Time to initiate roots: Approximately 15 days.

Root description: Density is dense and freely branching. Thin root thickness. White in color, not effectively measured with a color chart.

Time to produce a rooted young plant: Approximately 60 days.

PLANT

Plant type: Shrub.

Age of plant described: Approximately 2 years old.

Growth habit: Compact growth with good branching.

Pot size of plant described: #2 container.

Overall plant shape: Upright and Rounded.

Height: 60 cm.

Plant spread: 75 cm.

Growth rate: Medium.

Plant vigor: Strong.

Branching characteristics:

- *Length of primary lateral branches.*—37 cm.
- *Diameter of lateral branches.*—8.0 mm.
- *Quantity of lateral branches.*—38.

Stem:

- *Stem appearance.*—Round.
- *Stem strength.*—Strong.
- *Aspect.*—40° to 45°.
- *Color.*—Near RHS Yellow-Green 145B.
- *Pubescence.*—Yes.

Internode length: Range is 3.5 to 4.5 cm.

FOLIAGE

Leaf:

- *Arrangement.*—Opposite.
- *Leaf shape.*—Ovate-oblanceolate.
- *Average length.*—Approximately 5.7 cm.
- *Average width.*—Approximately 3.0 cm.
- *Apex.*—Acuminate-Acute.
- *Base.*—Cuneate-Attenuate.
- *Margin.*—Serrulate.
- *Texture of top surface.*—Slight pubescence.
- *Texture of bottom surface.*—Pubescent, to a greater extent than upper surface.
- *Color.*—Young foliage upper side: Near RHS Green 137A. Young foliage under side: Near RHS Green 138B. Mature foliage upper side: Near RHS Green 137A. Mature foliage under side: Near RHS Green 138B.
- *Venation.*—Pattern: Pinnate. Color upper side: Near RHS Green 145B. Color under side: Near RHS Green 145B.
- *Petiole.*—Length: 4.5 mm. Diameter: 2.0 mm. Petiole color upper side: Near RHS Green 145B. Petiole color lower side: Near RHS Green 145B. Petiole Texture: Pubescent.
- *Foliage durability.*—Very durable.

FLOWER

Natural flowering season: Late spring to summer.

Inflorescence type and habit: Umbel to panicle.

Inflorescence height: 9.0 cm.

Inflorescence width: 7.4 cm.

Flower longevity on plant: Individual flowers, 2 weeks.

Quantity of flowers per inflorescence: 15 to 20.

Quantity of flowers per plant: Hundreds.

Individual flowers:

- *Flower shape.*—Salverform.
- *Flower aspect.*—Upward and slightly outward.
- *Flowering arrangement.*—Single salverform flower.
- *Size.*—Diameter: Approximately 2.5 cm. Depth: Approximately 2.5 cm.
- *Other flower characteristics.*—Persistence: Self cleaning. Fragrance: Slight sweet scent.

Bud:

- *Shape.*—Obovate-spatulate.
- *Length.*—2.5 cm.
- *Diameter.*—1.0 cm.
- *Color.*—Near RHS White 155B.

Petal:

- *Petal arrangement.*—Whorled, fused at opening of throat.
- *Number of petals per flower.*—5.
- *Petal shape.*—Obovate.
- *Petal base.*—Fused at throat.
- *Margin.*—Entire, slightly undulate.
- *Tip shape.*—Obtuse.
- *Length.*—1.2 cm.
- *Width.*—1.0 cm.
- *Texture.*—Upper: Smooth. Lower: Smooth.
- *Color.*—When opening: Upper surface: Near RHS White 155B. Lower surface: Near RHS White 155B. Fully opened: Upper surface: Near RHS White 155B. Lower surface: Near RHS White 155B. Fades to: Near RHS White 155B.
- *Flower tube.*—Length: 2.2 cm. Diameter, base: 2.0 mm. Color: Near RHS White 155B blended with near RHS Yellow 12D.
- *Throat.*—Texture: Smooth. Color: Near RHS White 155B with a stripe of near RHS Yellow 13B.

Sepal:

- *Arrangement.*—Unguiculate, fused at base.
- *Appearance.*—Long, narrowly triangular.
- *Number.*—5.
- *Shape.*—Narrowly triangular.
- *Tip.*—Acute.
- *Base.*—Obtuse.
- *Margin.*—Entire.
- *Length.*—8 mm.
- *Width.*—1.5 mm.

*Texture, upper*.—Smooth, coriaceous.
*Texture, lower*.—Smooth, coriaceous.
*Color*.—Upper surface at maturity: Near RHS Yellow-Green 144B. Under surface at maturity: Near RHS Yellow-Green 144B.

Peduncle:
*Length*.—0.9 cm.
*Diameter*.—1.0 mm.
*Color*.—Near RHS Yellow-Green 145A.
*Orientation*.—Upright/outward.
*Strength*.—Good.
*Texture*.—Smooth, coriaceous, slightly pubescent.

Pedicel:
*Length*.—1.0 cm.
*Diameter*.—1.0 mm.
*Angle*.—Upright and outward.
*Strength*.—Good.
*Texture*.—Smooth, coriaceous, slightly pubescent.
*Color*.—Near RHS Yellow-Green 144B.

REPRODUCTIVE ORGANS

Stamens:
*Number*.—5.
*Filament length*.—3.0 cm.
*Filament color*.—Near RHS White 155B.

Anthers:
*Shape*.—Linear, slightly oblong.
*Length*.—5.0 mm.
*Color*.—Near RHS White 155B to near Greyed-Yellow 161D.
*Pollen color*.—Pollen production not observed.

Pistil:
*Number*.—1 per flower.
*Length*.—3.6 cm.
*Style*.—Length: 3.6 cm. Color: Near RHS White 155B fading to near RHS Yellow-Green 145B.
*Stigma*.—Color: Near RHS White 155B. Shape: Globular, flat-bottomed.

OTHER CHARACTERISTICS

Seeds and fruits: Not observed.

Disease/pest resistance: Neither resistance nor susceptibility to normal diseases and pests of *Weigela* have been observed except that the new cultivar has good mildew resistance.

Temperature tolerance: The new variety tolerates temperatures between −31° C. to 38° C.

Environmental stressors: Good resistance to wind and rain.

What is claimed is:

1. A new and distinct cultivar of *Weigela hybrida* plant named 'VUKOZ053929' as herein illustrated and described.

* * * * *